(12) United States Patent
Hsu

(10) Patent No.: US 8,357,386 B2
(45) Date of Patent: Jan. 22, 2013

(54) DRUG ELUTING COATINGS FOR MEDICAL IMPLANTS AND METHODS OF USE

(75) Inventor: Li-Chien Hsu, Mission Viejo, CA (US)

(73) Assignee: BIOTEGRA, Inc., Lake Forest, CA (US)

( * ) Notice: Subject to any disclaimer, the term of this patent is extended or adjusted under 35 U.S.C. 154(b) by 1420 days.

(21) Appl. No.: 11/119,075

(22) Filed: Apr. 28, 2005

(65) Prior Publication Data

US 2005/0191333 A1 Sep. 1, 2005

Related U.S. Application Data

(63) Continuation-in-part of application No. 10/423,718, filed on Apr. 26, 2003.

(60) Provisional application No. 60/405,933, filed on Aug. 26, 2002.

(51) Int. Cl.
*A61F 2/00* (2006.01)

(52) U.S. Cl. ........................................................ 424/423

(58) Field of Classification Search .................. None
See application file for complete search history.

(56) References Cited

U.S. PATENT DOCUMENTS

| | | | |
|---|---|---|---|
| 3,663,288 A | 5/1972 | Miller | |
| 4,613,665 A | 9/1986 | Larm | |
| 4,676,975 A | 6/1987 | McGary et al. | |
| 5,047,020 A | 9/1991 | Hsu | |
| 5,061,738 A | 10/1991 | Solomon et al. | |
| 5,112,457 A | 5/1992 | Marchant | |
| 5,288,711 A | 2/1994 | Mitchell et al. | |
| 5,356,433 A | 10/1994 | Rowland et al. | |
| 5,447,724 A | 9/1995 | Helmus et al. | |
| 5,455,040 A | 10/1995 | Marchant | |
| 5,464,650 A | 11/1995 | Berg et al. | |
| 5,496,832 A | 3/1996 | Armstrong | |
| 5,525,348 A | 6/1996 | Whitebourne et al. | |
| 5,529,986 A * | 6/1996 | Larsson et al. ................. | 514/54 |
| 5,609,629 A | 3/1997 | Fearnot et al. | |
| 5,665,728 A | 9/1997 | Morris et al. | |
| 5,716,981 A | 2/1998 | Hunter et al. | |
| 5,824,049 A | 10/1998 | Ragheb et al. | |
| 6,120,536 A | 9/2000 | Ding et al. | |
| 6,231,600 B1 | 5/2001 | Zhong | |
| 6,251,136 B1 | 6/2001 | Guruwaiya et al. | |

(Continued)

FOREIGN PATENT DOCUMENTS

WO WO 2005039443 A2 * 5/2005

OTHER PUBLICATIONS

Goods et al.; "Utilization of the Coronary Balloon-Expandable Coil Stent Without Anticoagulation or Intravascular Ultrasound;" Circulation; vol. 93, No. 10; May 15, 1996; pp. 1803-1808.

(Continued)

*Primary Examiner* — Paul Dickinson
(74) *Attorney, Agent, or Firm* — Blue Capital Law Firm, P.C.

(57) ABSTRACT

A drug coating for a medical device comprises one or more drug composite layers. The drug composite layer comprises one or more therapeutic agents dispersed within one or more modified bioactive binders. The modified bioactive binders are hydrophobic compounds bonded to bioactive binders, and the modified bioactive binders are not inert polymers.

2 Claims, 1 Drawing Sheet

U.S. PATENT DOCUMENTS

| | | |
|---|---|---|
| 6,273,913 B1 | 8/2001 | Wright et al. |
| 6,284,305 B1 * | 9/2001 | Ding et al. .................. 427/2.28 |
| 6,299,604 B1 | 10/2001 | Ragheb et al. |
| 6,306,166 B1 | 10/2001 | Barry et al. |
| 6,309,660 B1 | 10/2001 | Hsu et al. |
| 6,316,018 B1 | 11/2001 | Ding et al. |
| 6,335,029 B1 | 1/2002 | Kamath et al. |
| 6,344,035 B1 | 2/2002 | Chudzik et al. |
| 2001/0016611 A1 * | 8/2001 | Kashiwabara et al. ....... 523/112 |

OTHER PUBLICATIONS

Hermanson et al.; Immobilized Affinity Ligand Techniques; 1992; pp. 195-202; Academic Press.

LaBlanche et al.; "Combined antiplatelet therapy with ticlopidine and aspirin: A simplified approach to intracoronary stent management;" Eur Heart J; vol. 17; Sep. 1996; pp. 1373-1380.

Mak et al.; "Subacute Stent Thrombosis: Evolving Issues and Current Concepts;" J Am Coll Cardiol; vol. 27, No. 2; Feb. 1996; pp. 494-503.

Mehran et al.; "Angiographic Patterns of In-Stent Restenosis: Classification and Implications for Long-Term Outcome;" Circulation; vol. 100; Nov. 2, 1999; pp. 1872-1878.

Rogers et al.; "Inhibition of Experimental Neointimal Hyperplasia and Thrombosis Depends on the Type of Vascular Injury and the Site of Drug Administration;" Circulation; vol. 88, No. 3; Sep. 1993; pp. 1215-1221.

Schatz et al.; "Clinical Experience With the Palmaz-Schatz Coronary Stent: Initial Results of a Multicenter Study;" Circulation; vol. 83, No. 1; Jan. 1991; pp. 148-161.

Schwartz; "Characteristics of an Ideal Stent Based Upon Restonosis Pathology;" J Invas Cardiol; vol. 8, No. 8; Oct. 1996; pp. 386-387.

Serruys et al.; "Angiographic Follow-Up After Placement of a Self-Expanding Coronary-Artery Stent;" N. Eng J Med; vol. 324, No. 1; Jan. 3, 1991; pp. 13-17.

* cited by examiner

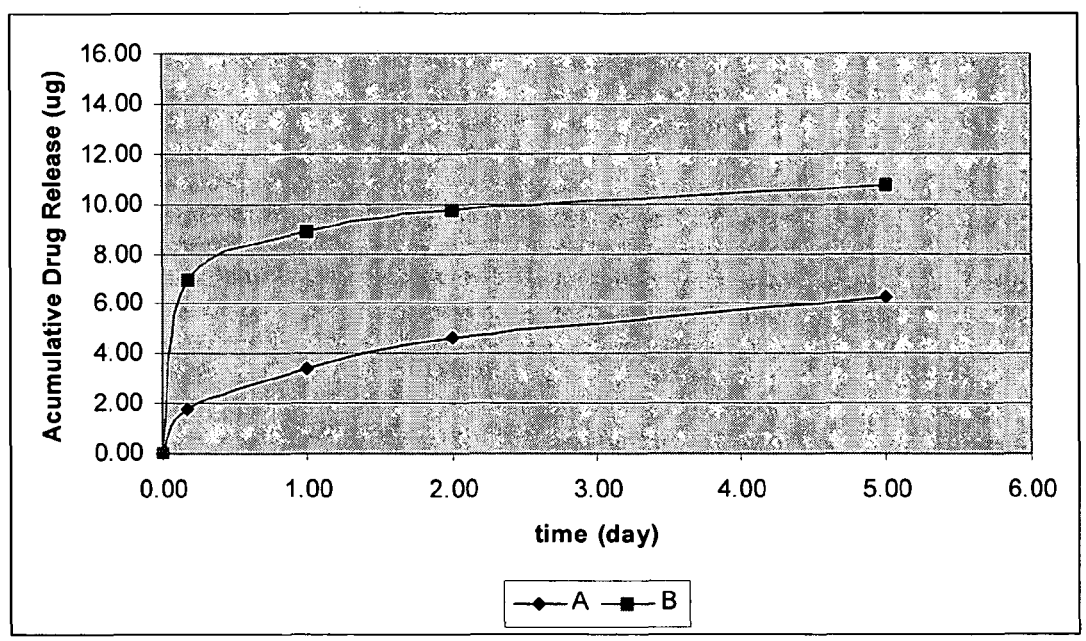

DRUG ELUTING COATINGS FOR MEDICAL IMPLANTS AND METHODS OF USE

CROSS REFERENCE TO RELATED APPLICATIONS

This application is a continuation-in-part of U.S. patent application Ser. No. 10/423,718, filed Apr. 26, 2003, which claims the benefit of U.S. Provisional Application No. 60/405,933, filed Aug. 26, 2002, and whose entire contents are hereby incorporated by reference.

BACKGROUND

The implantation or insertion of a medical device into a patient's body can cause the body to exhibit adverse physiological reactions. The reactions may range from infections to the formation of emboli or clots in blood vessels. One particularly adverse physiological reaction is the result of epithelial damage to the cardiovasculature. That is, the vasculature can be damaged during procedures such as percutaneous transluminal coronary angioplasty (PCTA). As a result of damage to the epithelium of the vasculature, a cascade of physiological events may result in the re-narrowing (restenosis) of the vessel. While not completely understood, restenosis may be the result of smooth muscle cell proliferation in the intimal layers of the vessel.

Restenosis of an artherosclerotic coronary artery after PTCA occurs in 10-50% of patients undergoing this procedure and subsequently requires either further angioplasty or coronary artery bypass graft. In order to maintain the patency of the vessel, intravascular stents have been developed as a mechanical means of preventing the collapse or abrupt closure of the dilated segment of the artery.

Compared to PTCA, coronary stenting has a reduced restenosis rate. The angiographic restenosis rate for coronary stenting is about 10 to 20% in short lesions and large vessels. In-stent restenosis, however, occurs in over 30% to 60% of patients with diabetes, diffuse lesions, or lesions that occur in small vessels or are located at a bifurcation (Mehran R, et al. Circulation 1999; 100:1872-8). It is known that stenting prevents restenosis by eliminating negative remodeling and elastic recoil. However, stents fail to prevent neointimal proliferative response due to vessel injury. Studies have shown that stent-induced neointimal formation is more extensive and protracted than that provoked by PTCA (Schwartz R S. J Invas Cardiol 1996; 8:386-7; Rogers C, et al. Circulation 1993; 88:1215-21). In particular, intimal hyperplasia is the major component of late lumen loss after stent implantation.

Despite a high rate of procedural success with stent implantation, an unacceptably high (approximately 25%) rate of stent thrombosis is also experienced (Serruys P W et al. N Engl J Med 1991; 324: 13-7; Schatz R A et al. Circulation 1991; 83:148-61). With the use of aggressive and precise anti-platelet and anti-coagulation therapy along with the implementation of high pressure balloon expansion, recent studies have shown thrombosis rates of less than 2% when stents are implanted electively and thrombosis rates of less than 5% in the treatment of abrupt closure (Lablanche J M, et al. Eur Heart J 1996; 17:1373-80; Goods C M, et al. Circulation 1996; 93:1803-8). Although thrombosis rates are lower as compared to the results from the early studies, stent thrombosis is a disastrous complication that carries a high risk of ischemic sequelae. For example, data from several trials show rates of myocardial infarction and death of 61% and 12%, respectively (Mak K H et al. J Am Coll Cardiol 1996; 2 7:494-503). Additionally, systemic anti-platelet and anti-coagulation therapy increases the incidence of bleeding complications. Accordingly, there still remains a need for solution to stent thrombosis.

One approach to improve the biocompatibility of stents is to incorporate bioactive or pharmacological agents onto the stents. Various techniques have been utilized to immobilize bioactive agents onto relatively inert surfaces of stents. One such technique involves coupling bioactive agents onto stent surfaces via covalent bonding. For example, U.S. Pat. No. 4,613,665 issued to Larm describes the coupling of heparin with reactive aldehyde groups to an aminated surface. Also, U.S. Pat. Nos. 5,112,457 and 5,455,040 issued to Marchant disclose the use of a similar approach to end-bind heparin on modified substrates. The substrate modification consists of depositing a film of plasma polymerized N-vinyl-2-pyrrolidone and attaching a spacer (such as PEG) on the film. The end group of the spacer is a primary amine, which can be bonded to aldehyde-ended heparin through reductive amination.

While useful, the covalent bonding approach has various shortcomings. For instance, this approach generally involves a series of chemical reactions performed directly on the surfaces of the device which only allows a single layer of bioactive agents to be attached to the surfaces. As a result, limited amounts of bioactive agents may be applied to the surface of the stent. Moreover, if excessive reagents or reactants are used in the covalent bonding process, stent functionality can be compromised by minimizing the stent's ability to be fully expanded. Also, release of such active agents from the stent surface may not be possible or very limited because the active agents are chemically bonded to the stent surface.

An alternative method to covalent bonding approach involves physically blending or dispersing bioactive agent(s) with inert polymers. These "inert" polymers do not possess any known pharmacological activity and only serve as a carrier or binder for the bioactive agent(s). For instance, bioactive compounds such as heparin have been applied to stent surfaces utilizing inert polymers such as thermoplastic polyurethane, silicone, polycaprolactone, polylactic acid, polyethylene-vinyl acetate and cellulose-based polymers.

The use of inert polymers in drug coatings permits larger doses of drugs to be applied to the medical device surface and concomitantly larger amounts of the drugs may be released. However, there remains the difficulty of combining multiple drugs having different physical properties. For example, a hydrophobic drug and a hydrophilic drug could not be concomitantly applied because they are not miscible. In order to incorporate such a drug combination, multiple chemical reaction steps, or multiple physical deposition steps including micronizing the drug for dispersion are necessary. These multiple reaction/deposition steps generally are cumbersome and costly. Furthermore, the uniformity of the drug coating and drug release rates are often difficult to control. Thus, there still remains a need for uniform drug coatings that are capable of controllably delivering multiple drugs to a site of injury.

SUMMARY

Embodiments of the drug releasing coatings described herein are uniform drug coatings capable of being applied to at least one surface of a medical device without the use of inert polymers. The disclosed embodiments of the drug releasing coatings do not require that the application of an inert polymer layer on the surface of the medical device to bind a therapeutic agent to the medical device surface. Rather, the drug releasing coatings described herein utilized biologically active binders to apply one or more therapeutic agents to at least one surface of a medical device.

In one embodiment, the drug coating comprises one or more drug composite layers. The drug composite layer comprises one or more therapeutic agents dispersed within one or more hydrophobic bioactive binders that are not inert polymers. In another embodiment, the drug coating further includes a means for controllably releasing the therapeutic agents and hydrophobic bioactive binders from one or more surfaces of the medical device.

In another embodiment, the drug coating comprises one or more therapeutic agents and a means for controllably releasing the therapeutic agents from one or more surfaces of the medical device. In this embodiment, the releasing means is applied over the one or more therapeutic agents.

Other features of the embodiments disclosed in this specification will become apparent from the following detailed description, which illustrates by way of example, the features of drug releasing coatings.

BRIEF DESCRIPTION OF THE DRAWINGS

FIG. 1 graphically depicts the drug release rates of two embodiments of the drug releasing coating.

DETAILED DESCRIPTION

Embodiments of the drug releasing coatings described herein and associated methods for their preparation can be used to deliver multiple drugs to a site of injury. Broadly, the coating compositions are composed of one or more modified, biologically active binders and at least one therapeutic agent dispersed in a substantially uniform manner within the binders. In one embodiment, the drug releasing coatings are capable of delivering anti-restenotic agents to a localized site within a patient's body while also providing anti-thrombotic, anti-inflammatory, and pro-healing properties to the medical device surface. Accordingly, thrombosis and restenosis associated with medical device implantation (such as stent implantation) can be minimized by devices incorporating the drug releasing coating described herein.

The embodiments of the drug releasing coatings comprise one or more therapeutic agents dispersed in one or more modified, biologically active binders. The bioactive binders are biologically active substances that are converted into a suitable binder by changing the hydrophobicity of the biologically active substance through chemical modification. Such chemical modification includes the attachment of hydrophobic groups onto the biologically active substances through ionic and/or covalent bonding.

According to one embodiment, suitable biologically active components that may be modified into bioactive binders include, but is not limited to, dextran sulfate, hirudin, or sulfated pectin. In another embodiment, the modified biologically active binder is a modified glycosaminoglycan complex. The glycosaminoglycan complexes are defined as "modified" as a chemical property—the hydrophilicity—of the glycosaminoglycan complex is altered. That is, in one embodiment, the glycosaminoglycan complexes are altered from hydrophilic complexes into hydrophobic complexes by substituting the counter ion with hydrophobic compounds associated with cations or cationic groups. Alternatively, the glycosaminoglycan complexes are altered into hydrophobic complexes by covalently attaching hydrophobic groups to the glycosaminoglycan complex. As those skilled in the art will appreciate, glycosaminoglycans are biologically active as they have been found to be anti-thrombotic, anti-restenotic, and anti-inflammatory. Furthermore, these modified complexes can be used to bind one or more therapeutic agents to the surface of a medical device. Non-limiting examples of glycosaminoglycans include, but are not limited to, heparin, heparinoids, hyaluronic acid, chondroitin sulfate, heparan sulfate, dermatan sulfate, and keratin sulfate.

According to one embodiment, the hydrophobic cationic containing compounds may be amine or amino compounds. In another embodiment, the hydrophobic compounds containing cationic groups may be tertiary ammonium salts. In another embodiment, hydrophobic cationic groups may be quaternary ammonium salts, such as, but not limited to, benzalkonium chloride, tridodecylmethyl ammonium chloride, stearylkonium chloride, cetylkonium chloride, and combinations thereof. In another embodiment, compounds containing hydrophobic cationic groups may be polylysine, protamine sulfate, hexadimethrine bromide, polyethylene imine, and polyhexamethylene biguanide.

According to another embodiment, the modified biologically active binder may be a modified heparin complex. As those skilled in the art will appreciate, heparin is normally hydrophilic and is typically complexed with such counter ions as, sodium, lithium, zinc, or calcium. These heparin complexes may be modified into hydrophobic complexes by substituting the sodium or calcium with hydrophobic cations. For instance, according to one embodiment, the hydrophobic cations may be tertiary ammonium complexes. In another embodiment, the hydrophobic cations may be quaternary ammonium salts, such as, but not limited to, benzalkonium chloride, tridodecylmethyl ammonium chloride, stearylkonium chloride, cetylkonium chloride, and combinations thereof. In another embodiment, compounds containing hydrophobic cationic groups may be polylysine, protamine sulfate, hexadimethrine bromide, polyethylene imine, and polyhexamethylene biguanide.

In yet another embodiment, the modified biologically active binder may be hydrophobically modified hirudin. Hirudin may be hydrophobically modified by reacting the amino acids on hirudin with hydrophobic compound(s). The side chains of amino acids 27 to 37 are particularly suitable for such modification as the modifications at these locations are less likely to affect the biological activity of hirudin. Coupling agents with spacer arms may also be used to react with the free N-terminal amino group, amino groups of the lysine side chains, amino groups of the histidines, amidine groups of the arginines. Hydrophobic groups such as, but not limited to, tyrosine, serine, or threonine side chains can also be chemically linked to the hydroxyl groups of hirudin. Generally, the hydrophobically modified hirudin has little or no loss of anti-thrombin activity as a result of the linkage of the hydrophobic groups to hirudin. Examples of hydrophobic compounds are long chain substituted and/or unsubstituted fatty acids, fatty alcohols, or fatty amines. Various coupling agents such as carbodiimides, tosyl chloride, and other agents can be used in peptide and protein immobilizations (Ref: Immobilized Affinity Ligand Techniques, Hermanson G T, et al, Academic Press Inc, 1992). In another embodiment, other peptide based anti-thrombotic or anti-platelet agents can be similarly modified to act as hydrophobic and pharmacologically active binders.

Because the modified biologically active binders are hydrophobic, these substances are soluble in organic solvents such as, but not limited to, halogenated hydrocarbons, aromatic and aliphatic hydrocarbons, alcohols, cyclic ethers, ketones, such as methylene chloride, ethanol, tetrahydrofuran and 1,1,2 trichloroethane. The choice of hydrophobic cationic groups depends on the hydrophobicity of the modified biologically active carrier desired and the nature of the antirestenotic agent to be incorporated. Other factors that affect the choice of the hydrophobic cation group include, but are not limited to, solubility, relative release rate of the antirestenotic agent and bioactive binder, and physical and chemical compatibility. The compatibility of the bioactive binder and the therapeutic agent is enhanced when the hydrophobicity of the modified binders "matches" (or is relatively similar to) that of therapeutic agent(s) to be incorporated. The enhanced compatibility leads to the formation of a homogenous mixture, which results in a uniform coating. Furthermore, enhanced compatibility between the bioactive binder and therapeutic agent provides a similar and predictable release rate for the active binder and the therapeutic agent upon exposure of the coating to physiological environment.

Consequently, any hydrophobic therapeutic agents may also be dissolved in common organic solvents with various embodiments of the modified biologically active binders. In one embodiment, the hydrophobic therapeutic agents include, but are not limited to, anti-inflammatory, anti-proliferative, anti-migratiory, anti-neoplastic, anti-restenotic, immunosuppressive agents, anti-platelet, or agents that promote healing and re-endothelialization. In one embodiment, the hydrophobic therapeutic agents include, but are not limited to, paclitaxel, rapamycin (sirolimus), everolimus, tacrolimus, actinomycin-D, dexamethasone, mycophenolic acid, cyclosporins, estradiol, ticlopidine, clopidogrel, breviscapinum, prasugrel, analogs and derivatives thereof, or combinations thereof. Accordingly, both the biologically active binders and the therapeutic agents can be concomitantly applied to the surface of a medical device. Furthermore, the relative ratio of the binders to the therapeutic agent can be easily varied depending on the type of medical devices and anticipated pathophysiological problems associated with the implant devices.

The ability to eliminate inert polymer carrier enhances the bioactivity of the coating composition and minimizes potential adverse physiological reactions to the inert polymer carrier. The composition also minimizes the thickness of coating thereby limiting the impact of coating on profile of the coated devices. The composition also allows for the incorporation of two distinctly different pharmacological agents (e.g., an antithrombotic agent and an anti-angiogenic agent) onto/into the prostheses in one step. Thus, the various embodiments of drug coatings avoid the necessity of multiple chemical reaction steps or multiple physical deposition steps that are generally required to incorporate the two types of pharmacological agents. Embodiments disclosed herein further provide compositions and methods that avoid the need for micronizing glycosaminoglycans in order to incorporate them with hydrophobic therapeutic agents.

In another embodiment, the drug composite (comprising modified biologically active binders and one or more therapeutic agents) includes a cap coat. The cap coat layer is applied over the drug composite to regulate the release of the therapeutic drug from the surface of a medical device. In another embodiment, the cap coat layer comprises one or more layers of a modified biologically active binder applied over the drug composite. In one embodiment, the modified biologically active binder used to form the cap coating is the same binder used in the drug composite. In another embodiment, the binder used in the cap coating is different from the binder used in the drug composite.

In another embodiment, the cap coat layer comprises one or more layers of biostable or bioabsorbable polymers. According to one embodiment, the cap coating may be composed of ethylene vinyl acetate copolymers. In another embodiment, the cap coating may be composed of polyalkylmethacrylate, wherein the alkyl group may be one to eight carbon atoms. For instance, the cap coating may be composed of one or more layers of polybutylmethacrylate. In another embodiment, the cap coating may be composed of copolymers of ethylene and alkylacrylate, wherein the alkyl group may be one to eight carbon atoms. In yet another embodiments, the cap coating may be composed of polyurethanes, copolymers of ethylene and propylene, styrene butadiene rubber, or silicone based polymers. As those skilled in the art will appreciate, the cap coating has elastomeric properties that allow the cap coating to be applied to expandable or flexible medical devices. Accordingly, the elastic properties of the cap coating permits the coating to be expanded and flexed without comprising the integrity of the cap coating thereby allowing for the controlled the release of the therapeutic agents (and biologically active binders) from the surface of the medical device. For non-flexible and non-expandable medical devices, non-elastomeric materials such as polylactide can be used as a cap coating.

In another embodiment, the cap coat layer comprises one or more layers of a combination of a modified biologically active binder and a biostable or a bioabsorbable polymer. As those skilled in the art will appreciate, the proportion of bioactive binder and the polymer may be varied upon the desired release rate. As shown in example 14, cap coatings incorporating a bioactive binder with a polymer can alter the release rate of the therapeutic agent.

The biostable polymers generally considered to be biocompatible include, but are not limited to, polyurethanes, silicones, ethylene-vinyl acetate copolymer, polyethers such as homopolymers or copolymers of alkylene oxide, homo- or copolymers of acrylic, polyamides, polyolefins, polyesters, polydienes, cellulose and related polymers.

The bioabsorbable polymers include, but are not limited to, poly(L-lactic acid), polycaprolactone, poly(lactide-co-glycolide), poly(hydroxybutyrate), poly(hydroxybutyrate-covalerate), polydioxanone, polyorthoester, polyanhydride, poly(glycolic acid), poly(D,L-lactic acid), poly(glycolic acid-cotrimethylene carbonate), polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid.

As those skilled in the art will appreciate, these biostable and bioabsorbable polymers and other polymer systems can be used if they can be dissolved or dispersed in a solvent system that can be applied to the drug composite without causing adverse effect on the composite. Generally, conventional coating techniques, such as spray-coating, dip-coating, or brush-coating can be employed to apply the polymer coating.

In another aspect, various methods can be used to apply the drug coatings onto one or more surfaces of the medical device. In one method, a composite drug coating solution is prepared by dissolving appropriate amounts of therapeutic agent and biologically active binders in a common organic solvent. According to one method, the coating solution can be applied on a device, such as stent, by spray coating. After the solvent in the coating solution is evaporated, a thin layer of coating remains on the surface of the device. The process can be repeated as many times as desired. As those skilled in the art will appreciate, a waiting period may or may not be required, depending on the volatility of the solvent system used.

Alternatively, the coating can also be applied to the medical device by dip-coating. Dip-coating is especially useful for devices that are not conducive to being spray-coated such as, but not limited to, vascular grafts and stent grafts. Brush-coating is another method of applying the coating solution (comprising at least one therapeutic agent and biologically active binder) to the surface of a medical device. A swab saturated with coating solution can be applied to the devices. As those skilled in the art will appreciate, the coating may be applied to the device surface by using a combination of spraying, dipping, and brushing.

In another aspect, additional embodiments are directed to medical devices having one or more drug releasing coatings applied to at least one surface of the medical device. In one embodiment, one or more cap coating layers may be applied over the drug releasing coatings. The drug releasing coatings are capable of releasing at least one therapeutic agent while imparting anti-thrombotic properties to the surface of the medical devices. The coated medical devices include expandable prostheses such as, but not limited to, balloon expandable stents and self-expanding stents, stent grafts, vascular grafts, heart valves, heart valve sewing rings, annuloplasty rings, venous valves, sutures, sutureless coronary anastomosis devices connectors, implantable catheters and shunts, and other access devices. Alternatively, the compositions disclosed herein can also be incorporated into the bulk materials from which the prostheses are constructed.

In one embodiment, the medical device includes one or more layers of a drug releasing coating. According to one embodiment, the various layers of drug releasing coating comprise the same modified bioactive binder. Alternatively, the various layers of the drug releasing coating may have different modified bioactive binders. For instance, modified hirudin may be the binder in one layer of the drug releasing coating and sulfated pectin may be the binder for another layer of the drug releasing coating. In another embodiment, the drug releasing coating comprises one or more modified bioactive binders. In other embodiments, the therapeutic agents are the same in each of the drug releasing layers. Alternatively, the therapeutic agents are different in each of the drug releasing layers.

In another embodiment, the medical device includes one or more layers of a drug releasing coating and one or more cap coating layers applied over the drug releasing coating. In one embodiment, the medical device includes a first drug releasing coating layer followed by a first cap coat layer and a second drug releasing coating layer followed by a second cap coat layer. Accordingly, there are alternating layers of drug and cap coats in this embodiment.

In another embodiment, the medical device includes one or more drug releasing layers followed by one or more cap coat layers. For instance, in one embodiment, the medical device can have the following cross-section (moving away from the device surface): medical device—one or more drug layers—one or more cap coat layers—one or more drug layers—one or more cap coat layers. As those skilled in the art will appreciate, various sequential layering of the drug releasing coating and the cap coating are contemplated and within the scope of the embodiments disclosed herein.

In one embodiment, the medical device includes one or more layers of one or more therapeutic agents applied to at least one surface of the medical device followed by one or more cap coat layers. In this embodiment, the therapeutic agents are "trapped" on the surface of the medical device by the cap coat layer(s). In another embodiment, medical device includes one or more layers of therapeutic agents and the cap coat sequentially layered on the surface of the medical device.

In another aspect, methods of minimizing restenosis and thrombosis are disclosed herein. According to one exemplary method, the medical implant is provided with at least one uniform coating that is composed of a modified glycosaminoglycan complex and at least one therapeutic agent such as paclitaxel, rapamycin (sirolimus), tacrolimus, everolimus, actinomycin-D, dexamethasone, mycophenolic acid, cyclosporins, estradiol, ticlopidine, clopidogrel, prasugrel, breviscapinum, or combinations thereof. The medical implant having the drug releasing coating may be delivered and implanted at a desired site within the patient's body by any method known or developed in the art. Once implanted, the therapeutic agents and/or the modified glycosaminoglycan complexes may be controllably released from the surface of the medical implant to minimize restenosis and thrombosis.

While several embodiments have been described, those skilled in the art will appreciate that various substitutions, omissions, modifications and changes which may be made without departing from the scope or spirit of the embodiments disclosed herein. Accordingly, it is intended that the foregoing description be considered merely exemplary and not a limitation thereof. A further understanding of the drug releasing coatings and associated methods will be afforded to those skilled in the art from the following non-limiting examples.

EXAMPLE 1

Paclitaxel and Stearylkonium Heparin

Paclitaxel (Sigma Aldrich, St. Louis, Mo.) and stearylkonium heparin (as prepared according to U.S. Pat. No. 5,047,020, whose entire contents are incorporated by reference) at a weight ratio of 50/50 were dissolved in methylene chloride. The coating solution was then sprayed onto the surface of a 9 mm long balloon expandable stainless steel coronary stent. The spraying was conducted in such a way that substantial all exposed surfaces of the stent were covered with the solution and that a desired amount of drug loading on the stent was achieved. The coated stent was then dried in an oven at about 50° C. for 2 hours or until all solvent is evaporated. The coverage of coating on the surfaces of the stent was examined by using heparin or a cation sensitive dye.

EXAMPLE 2

Paclitaxel and Benzalkonium Heparin

Paclitaxel (Sigma Aldrich, St. Louis, Mo.) and benzalkonium heparin at a weight ratio of 75/25 were dissolved in ethanol. A 9 mm long balloon expandable stainless steel coronary stent mount on a mandrel was then dip-coated in the solution. The coated stent was then rotated on the mandrel at a low rpm until all solvent was evaporated. Slow rotation while drying ensures an even distribution of the drug components. The dip-coating steps can be repeated until a desirable drug loading is accomplished.

EXAMPLE 3

Dexamethasone and Tridodecylmethyl Ammonium Heparin

Dexamethasone and tridodecylmethyl ammonium heparin (TDMAC heparin) at a weight ratio of 25/75 were dissolved in tetrahydrofuran. The coating solution was then sprayed onto the surface of a balloon expandable stainless steel coronary stent. The spraying was conducted in such a way that substantial all exposed surfaces of the stent were covered with the solution and that a desired amount of drug loading on the stent was achieved. The coated stent was then dried in an oven at about 50° C. for 2 hours or until all solvent is evaporated. The coverage of coating on the surfaces of the stent was examined by using heparin or cation sensitive dye.

EXAMPLE 4

Paclitaxel and Chondroitin Sulfate Complex

Paclitaxel and a complex prepared from stearyldimethylbenzyl ammonium chloride and chondoitin sulfate at a weight ratio of 25/75 was dissolved in methylene chloride. The stent was mounted on a rotating mandrel. The coating solution was then sprayed onto the stent while the stent was being rotated until a uniform layer of the coating was deposited. The coated stent was then dried in an oven at about 50° C. for 2 hours or until all solvent is evaporated.

EXAMPLE 5

Paclitaxel and Dermatan Sulfate Complex

Paclitaxel and a complex prepared from stearyldimethylbenzyl ammonium chloride and dermatan sulfate was dissolved in methylene chloride at a weight ratio of 20/80. The stent was mounted on a rotating mandrel. The coating solution was then sprayed onto the stent while the stent was being rotated until a uniform layer of the coating was deposited. The coated stent was then dried in an oven at about 50° C. for 2 hours or until all solvent is evaporated.

EXAMPLE 6

Rapamycin and Benzalkonium Heparin

Rapamycin and benzalkonium heparin at a weight ratio of 50/50 were dissolved in 1,1,2 trichloroethane. The coating solution was then sprayed onto the surface of a balloon expandable stainless steel coronary stent. The spraying was conducted in such a way that substantial all exposed surfaces of the stent were covered with the solution and that a desired amount of drug loading on the stent was achieved. The coated stent was then dried in an oven at about 50 C for 2 hours or until all solvent is evaporated. The coverage of coating on the surfaces of the stent was examined by using heparin or cation sensitive dye.

EXAMPLE 7

Top Coat (Stearylkonium Heparin)

An appropriate amount of stearylkonium heparin was dissolved in methylene chloride to yield a 2% (wt/vol) solution. The solution was sprayed to the stent prepared according to that described in example 1 until a thin layer of top coat is uniformly deposited on the drug-coated stent. The coated stent was then dried until all solvent is evaporated.

EXAMPLE 8

Top Coat (Ethylene Vinyl Acetate Copolymer)

An appropriate amount of ethylene vinyl acetate copolymer was dissolved in methylene chloride to yield a 2.5% (wt/vol) polymer solution. The solution was sprayed to the stent prepared according to that described in example 4 until a thin layer of top coat is uniformly deposited on the drug-coated stent. The coated stent was then dried until all solvent is evaporated.

EXAMPLE 9

Top Coat (Polycaprolactone)

An appropriate amount of polycaprolactone was dissolved in methylene chloride to yield a 5% (wt/vol) polymer solution. The solution was sprayed to the stent prepared according to that described in Example 1 until a thin layer of cap coat is uniformly deposited on the drug-coated stent. The coated stent was then dried until all solvent is evaporated.

EXAMPLE 10

Paclitaxel (Sigma Aldrich, St. Louis, Mo.) and stearylkonium heparin at a weight ratio of 50/50 were dissolved in methylene chloride. An expanded ePTFE stent graft is immersed in the solution briefly and dried subsequently to evaporate off the solvent. The coated stent graft is then briefly dipped in a polymer solution containing ethylene vinyl acetate copolymer and subsequently dried.

EXAMPLE 11

Rapamycin and benzalkonium heparin at a weight ratio of 25/75 were dissolved in 1,1,2 trichloroethane. A polyester knit suture ring for heart valve is dip-coated in the solution and dried. The coated suture ring is then dip-coated in biodegradable elastomeric copolymer of caprolactone and glycolic acid in acetone (5%, wt/vol) and subsequently dried.

EXAMPLE 12

Top Coat (Polyalkymethacrylate)

An appropriate amount of polyalkymethacrylate is dissolved in toluene to give a 2% (wt/vol) solution. The solution was sprayed to the stent prepared according to that described in example 1 until a thin layer of top coat is uniformly deposited on the drug-coated stent. The coated stent was then dried until all solvent is evaporated.

EXAMPLE 13

Top Coat

An appropriate amount of polyalkymethacrylate and stearylkonium heparin is dissolved in a mixture of toluene and alcohol to give a 2% (wt/vol) solution. The solution was sprayed to the stent prepared according to that described in example 1 until a thin layer of top coat is uniformly deposited on the drug-coated stent. The coated stent was then dried until all solvent is evaporated.

EXAMPLE 14

Drug Release Rate

Stents prepared according to that described in examples 12 (stent group A) and 13 (stent group B) are exposed to a mixture of saline and polysorbate surfactant at 37° C. The amount of paclitaxel released was analyzed using HPLC (supelcosil LC-F in a mixture of water and acetonitrile). The results shown in FIG. 1 demonstrate the ability for the polymer to regulate the drug release rate as well as the ability for the mixture of polymer and bioactive binder to further program the drug release rate.

What is claimed is:

1. A drug coating, comprising:
a uniform dispersion of one or more anti-restenotic agents and one or more hydrophobically-modified bioactive binders, wherein the hydrophobically-modified bioactive binders are the only binders in the uniform dispersion, and the hydrophobically-modified bioactive binders are water insoluble and act as a carrier for the anti-restenotic agents, the hydrophobically-modified bioactive binders including a positively-charged amine compound ionically-bonded to a glycosaminoglycan,
wherein the anti-restenotic agents are elutable from the drug coating and the glycosaminoglycan is elutable from the drug coating, and
wherein the positively-charged amine compound is a tertiary amine, quaternary amine, polylysine, protamine sulfate, hexadimethrine bromide, polyethylene imine, or polyhexamethylene biguanide.

2. The drug coating of claim 1, wherein the anti-restenotic agent is paclitaxel, rapamycin, tacrolimus, everolimus, actinomycin-D, or combinations thereof.

* * * * *